United States Patent [19]

Schwan

[11] 4,003,900
[45] Jan. 18, 1977

[54] 1-BENZYL-5-CHLORO-2-(1H)-PYRIMI-DONE

[75] Inventor: Thomas J. Schwan, Norwich, N.Y.

[73] Assignee: Morton-Norwich Products, Inc., Norwich, N.Y.

[22] Filed: Mar. 11, 1976

[21] Appl. No.: 666,024

[52] U.S. Cl. .............................. 260/251 R; 424/251
[51] Int. Cl.² ....................................... C07D 239/22
[58] Field of Search ................................ 260/251 R

[56] References Cited
UNITED STATES PATENTS

| | | | |
|---|---|---|---|
| 3,681,349 | 8/1972 | Schwan | 260/251 R |
| 3,833,586 | 9/1974 | Schwan | 260/251 R |

*Primary Examiner*—Lewis Gotts
*Assistant Examiner*—Dolph H. Torrence
*Attorney, Agent, or Firm*—Anthony J. Franze

[57] ABSTRACT

1-Benzyl-5-chloro-2(1H)-pyrimidone possesses pharmacological activity as an antianxiety agent.

1 Claim, No Drawings

1-BENZYL-5-CHLORO-2-(1H)-PYRIMIDONE

This invention relates to chemical compounds. In particular it is concerned with a compound of the formula:

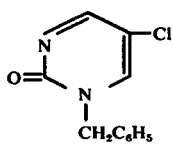

which possesses pharmacological activity affecting the central nervous system. When administered perorally to animals it exhibits antianxiety activity. This antianxiety action is evidenced in the control of pentylenetetrazol induced tonic extensor seizures in mice. An oral dose of 50 mg/kg of this compound to mice intravenously receiving 45 mg/kg of pentylenetetrazol counteracts the effects of pentylenetetrazol.

In order that this invention may be readily available to and understood by those skilled in the art, the following example is illustrated:

1-BENZYL-5-CHLORO-2(1H)-PYRIMIDONE

A 45 g (0.27 mole) portion of 5-chloro-2(1H)-PYRIMIDONE hydrochloride in 700 ml of methanol was treated with 57.5 g. (0.54 mole) of $Na_2CO_3$, 19.5 g (0.13 mole) of NaI and 34.5 g (0.27 mole) of benzyl chloride. The reaction mixture was refluxed for 19 hrs and concentrated to dryness under reduced pressure. The solid was partitioned between 300 ml of $H_2O$ and 700 ml of $CHCl_3$. The two phase system was filtered. The light tan solid was washed with ether and dried, m.p. 178°–181°. Yield: 17 g (28%).

The organic layer of the filtrate was separated, dried over $MgSO_4$ and filtered. The filtrate was concentrated to dryness under reduced pressure to give 41 g (68%) a light tan solid, m.p. 197°–199°.

The two crops were combined (total wt. 58 g) and recrystallized from 700 ml of acetonitrile, washed with acetonitrile, ether and air dried to give a cream solid, m.p. 200°–202°. Yield: 40 g (67%).

An analytical sample, m.p. 198°–200°, was obtained by recrystallization from acetonitrile.

Anal. Calcd. for $C_{11}H_9ClN_2O$: C, 59.87; H, 4.11; N, 12.70 found: C, 59.62; H, 4.04; N, 12.73

What is claimed is:

1. A compound of the formula:

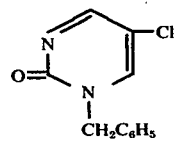

* * * * *